United States Patent
Lin et al.

(10) Patent No.: US 7,204,876 B2
(45) Date of Patent: *Apr. 17, 2007

(54) CALCIUM PHOSPHATE CEMENTS MADE FROM (TTCP) WITH SURFACE WHISKERS AND PROCESS FOR PREPARING SAME

(75) Inventors: Jiin-Huey Chern Lin, Winnetka, IL (US); Chien-Ping Ju, Carbondale, IL (US); Wen-Cheng Chen, Tainan Hsien (TW)

(73) Assignee: Calcitec, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/133,165

(22) Filed: May 19, 2005

(65) Prior Publication Data
US 2005/0274286 A1 Dec. 15, 2005

Related U.S. Application Data

(63) Continuation of application No. 10/773,701, filed on Feb. 6, 2004, which is a continuation-in-part of application No. 10/607,023, filed on Jun. 27, 2003, now Pat. No. 6,960,249, which is a continuation-in-part of application No. 10/414,582, filed on Apr. 16, 2003, now Pat. No. 7,094,282, which is a continuation-in-part of application No. 09/615,384, filed on Jul. 13, 2000, now abandoned.

(51) Int. Cl.
C04B 12/02 (2006.01)
(52) U.S. Cl. .................. 106/35; 106/690; 428/403; 428/404
(58) Field of Classification Search ............... 423/403, 423/315; 106/35, 690; 428/403, 404
See application file for complete search history.

(56) References Cited

U.S. PATENT DOCUMENTS 3,679,360 A 7/1972 Rubin et al.
4,371,484 A 2/1983 Inukai et al.

(Continued)

FOREIGN PATENT DOCUMENTS

JP 06-228011 8/1994

(Continued)

OTHER PUBLICATIONS

Sugawara et al., "Calcium Phosphate Cement: An In Vitro study of Dentin Hypersensitivity", The Journal of the Japanese Society for Dental Materials and Devices, 1989, vol. 8, pp. 282-294, no month.

(Continued)

*Primary Examiner*—Wayne A. Langel
(74) *Attorney, Agent, or Firm*—Meyertons, Hood, Kivlin, Kowert & Goetzel, P.C.; Eric B. Meyertons

(57) ABSTRACT

A tetracalcium phosphate (TTCP) particle for use in preparing a fast-setting, bioresorbable calcium phosphate cement is disclosed. The TTCP particle has a basic calcium phosphate whiskers on a surface thereof; the basic calcium phosphate whiskers having a Ca/P molar ratio greater than 1.33, and having a length up to about 5000 nm and a width up to about 500 nm. The basic calcium phosphate whiskers are substantially free of a hydroxyapatite phase and mainly composed of TTCP phase.

22 Claims, 3 Drawing Sheets

U.S. PATENT DOCUMENTS

| | | |
|---|---|---|
| 4,481,175 A | 11/1984 | Iino et al. |
| 4,518,430 A | 5/1985 | Brown et al. |
| 4,553,272 A | 11/1985 | Mears |
| 4,612,053 A | 9/1986 | Brown et al. |
| 4,623,553 A | 11/1986 | Ries et al. |
| RE33,161 E | 2/1990 | Brown et al. |
| RE33,221 E | 5/1990 | Brown et al. |
| 4,950,295 A | 8/1990 | Weigum et al. |
| 4,959,104 A | 9/1990 | Iino et al. |
| 5,017,518 A | 5/1991 | Hirayama et al. |
| 5,053,212 A | 10/1991 | Constantz et al. |
| 5,092,888 A | 3/1992 | Iwamoto et al. |
| 5,149,368 A | 9/1992 | Liu et al. |
| 5,152,791 A | 10/1992 | Hakamatsuka et al. |
| 5,164,187 A | 11/1992 | Constantz et al. |
| 5,180,426 A | 1/1993 | Sumita |
| 5,218,035 A | 6/1993 | Liu |
| 5,262,166 A | 11/1993 | Liu et al. |
| 5,336,264 A | 8/1994 | Constanz et al. |
| 5,338,356 A | 8/1994 | Hirano et al. |
| 5,342,441 A | 8/1994 | Mandai et al. |
| 5,409,982 A | 4/1995 | Imura et al. |
| 5,470,803 A | 11/1995 | Bonfield et al. |
| 5,476,647 A | 12/1995 | Chow et al. |
| 5,492,768 A | 2/1996 | Okimatsu et al. |
| 5,496,399 A | 3/1996 | Ison et al. |
| 5,503,164 A | 4/1996 | Friedman |
| 5,522,893 A | 6/1996 | Chow et al. |
| 5,525,148 A | 6/1996 | Chow et al. |
| 5,536,575 A | 7/1996 | Imura et al. |
| 5,542,973 A | 8/1996 | Chow et al. |
| 5,545,254 A | 8/1996 | Chow et al. |
| 5,550,172 A | 8/1996 | Regula et al. |
| 5,569,490 A | 10/1996 | Imura et al. |
| 5,605,713 A | 2/1997 | Boltong |
| 5,607,685 A | 3/1997 | Cimbollek et al. |
| 5,652,016 A | 7/1997 | Imura et al. |
| 5,683,461 A | 11/1997 | Lee et al. |
| 5,683,496 A | 11/1997 | Ison et al. |
| 5,695,729 A | 12/1997 | Chow et al. |
| 5,697,981 A | 12/1997 | Ison et al. |
| 5,702,449 A | 12/1997 | McKay |
| 5,766,669 A | 6/1998 | Pugh et al. |
| 5,782,971 A | 7/1998 | Constantz et al. |
| 5,814,681 A | 9/1998 | Hino et al. |
| 5,820,632 A | 10/1998 | Constantz et al. |
| 5,846,312 A | 12/1998 | Ison et al. |
| 5,891,448 A | 4/1999 | Chow et al. |
| 5,899,939 A | 5/1999 | Boyce et al. |
| 5,954,867 A | 9/1999 | Chow et al. |
| 5,958,430 A | 9/1999 | Campbell et al. |
| 5,964,932 A | 10/1999 | Ison et al. |
| 5,976,234 A | 11/1999 | Chow et al. |
| 5,993,535 A | 11/1999 | Sawamura et al. |
| 5,997,624 A | 12/1999 | Chow et al. |
| 6,005,162 A | 12/1999 | Constantz |
| 6,013,591 A | 1/2000 | Ying et al. |
| 6,013,853 A | 1/2000 | Athanasiou et al. |
| 6,027,742 A | 2/2000 | Lee et al. |
| 6,077,989 A | 6/2000 | Kandel et al. |
| 6,083,229 A | 7/2000 | Constantz et al. |
| 6,117,456 A | 9/2000 | Lee et al. |
| 6,118,043 A | 9/2000 | Nies et al. |
| 6,123,731 A | 9/2000 | Boyce et al. |
| 6,132,463 A | 10/2000 | Lee et al. |
| 6,162,258 A | 12/2000 | Scarborough et al. |
| 6,277,149 B1 | 8/2001 | Boyle et al. |
| 6,294,041 B1 | 9/2001 | Boyce et al. |
| 6,294,187 B1 | 9/2001 | Boyce et al. |
| 6,312,468 B1 | 11/2001 | Best et al. |
| 6,323,146 B1 | 11/2001 | Pugh et al. |
| 6,325,987 B1 | 12/2001 | Sapieszko et al. |
| 6,325,992 B1 | 12/2001 | Chow et al. |
| 6,332,779 B1 | 12/2001 | Boyce et al. |
| 6,340,648 B1 | 1/2002 | Imura et al. |
| 6,379,453 B1 | 4/2002 | Lin et al. |
| 6,440,444 B2 | 8/2002 | Boyce et al. |
| 6,458,162 B1 | 10/2002 | Koblish et al. |
| 6,478,825 B1 | 11/2002 | Winterbottom et al. |
| 6,495,156 B2 | 12/2002 | Wenz et al. |
| 6,530,955 B2 | 3/2003 | Boyle et al. |
| 6,533,821 B1 | 3/2003 | Lally |
| 6,547,866 B1 | 4/2003 | Edwards et al. |
| 6,569,489 B1 | 5/2003 | Li |
| 6,582,672 B1 | 6/2003 | Bonfield et al. |
| 6,585,946 B1 | 7/2003 | Bonfield et al. |
| 6,585,992 B2 | 7/2003 | Pugh et al. |
| 6,616,742 B2 | 9/2003 | Lin et al. |
| 6,648,960 B1 | 11/2003 | Lin et al. |
| 6,670,293 B2 | 12/2003 | Edwards et al. |
| 6,696,073 B2 | 2/2004 | Boyce et al. |
| 6,719,989 B1 | 4/2004 | Matsushima et al. |
| 6,752,831 B2 | 6/2004 | Sybert et al. |
| 6,793,725 B2 | 9/2004 | Chow et al. |
| 6,808,561 B2 | 10/2004 | Genge et al. |
| 6,808,585 B2 | 10/2004 | Boyce et al. |
| 6,840,995 B2 | 1/2005 | Lin et al. |
| 6,929,692 B2 | 8/2005 | Tas |
| 6,953,594 B2 | 10/2005 | Lee et al. |
| 6,955,716 B2 | 10/2005 | Xu et al. |
| 6,960,249 B2 | 11/2005 | Lin et al. |
| 6,994,726 B2 | 2/2006 | Lin et al. |
| 2002/0019635 A1 | 2/2002 | Wenstrom, Jr. et al. |
| 2002/0073894 A1 | 6/2002 | Genge et al. |
| 2002/0137812 A1 | 9/2002 | Chow et al. |
| 2002/0169066 A1 | 11/2002 | Cassidy et al. |
| 2003/0019396 A1 | 1/2003 | Edwards et al. |
| 2003/0031698 A1 | 2/2003 | Roeder et al. |
| 2003/0055512 A1 | 3/2003 | Genin et al. |
| 2003/0074081 A1 | 4/2003 | Ayers et al. |
| 2003/0078317 A1 | 4/2003 | Lin et al. |
| 2003/0120351 A1 | 6/2003 | Tofighi |
| 2003/0121450 A1 | 7/2003 | Lin et al. |
| 2003/0167093 A1 | 9/2003 | Xu et al. |
| 2003/0216777 A1 | 11/2003 | Lin et al. |
| 2004/0003757 A1 | 1/2004 | Chern Lin et al. |
| 2004/0022825 A1 | 2/2004 | Lagow |
| 2004/0031420 A1 | 2/2004 | Lin et al. |
| 2004/0076685 A1 | 4/2004 | Tas |
| 2004/0137032 A1 | 7/2004 | Wang |
| 2004/0175320 A1 | 9/2004 | Lin et al. |
| 2004/0180091 A1 | 9/2004 | Lin |
| 2004/0185181 A1 | 9/2004 | Matsumoto |
| 2004/0186481 A1 | 9/2004 | Chern Lin et al. |
| 2005/0029701 A1 | 2/2005 | Lin et al. |
| 2005/0069479 A1 | 3/2005 | Lin et al. |
| 2005/0076813 A1 | 4/2005 | Lin et al. |
| 2005/0101964 A1 | 5/2005 | Lin et al. |
| 2005/0184417 A1 | 8/2005 | Lin et al. |
| 2005/0184418 A1 | 8/2005 | Lin et al. |
| 2005/0186353 A1 | 8/2005 | Lin et al. |
| 2005/0186354 A1 | 8/2005 | Lin et al. |
| 2005/0186449 A1 | 8/2005 | Lin et al. |
| 2005/0263919 A1 | 12/2005 | Lin et al. |
| 2005/0263920 A1 | 12/2005 | Lin et al. |
| 2005/0263921 A1 | 12/2005 | Lin et al. |
| 2005/0263922 A1 | 12/2005 | Lin et al. |
| 2005/0263927 A1 | 12/2005 | Lin et al. |
| 2005/0263928 A1 | 12/2005 | Lin et al. |
| 2005/0263929 A1 | 12/2005 | Lin et al. |
| 2005/0263930 A1 | 12/2005 | Lin et al. |
| 2005/0263931 A1 | 12/2005 | Lin et al. |
| 2005/0267587 A1 | 12/2005 | Lin et al. |
| 2005/0267588 A1 | 12/2005 | Lin et al. |

| | | |
|---|---|---|
| 2005/0267589 A1 | 12/2005 | Lin et al. |
| 2005/0267593 A1 | 12/2005 | Lin et al. |
| 2005/0267604 A1 | 12/2005 | Lin et al. |
| 2005/0268819 A1 | 12/2005 | Lin et al. |
| 2005/0268820 A1 | 12/2005 | Lin et al. |
| 2005/0268821 A1 | 12/2005 | Lin et al. |
| 2005/0271740 A1 | 12/2005 | Lin et al. |
| 2005/0271741 A1 | 12/2005 | Lin et al. |
| 2005/0271742 A1 | 12/2005 | Lin et al. |
| 2005/0274282 A1 | 12/2005 | Lin et al. |
| 2005/0274287 A1 | 12/2005 | Lin et al. |
| 2005/0274288 A1 | 12/2005 | Lin et al. |
| 2005/0274289 A1 | 12/2005 | Lin et al. |
| 2005/0279252 A1 | 12/2005 | Lin et al. |
| 2005/0279256 A1 | 12/2005 | Lin et al. |
| 2006/0011099 A1 | 1/2006 | Lin et al. |
| 2006/0011100 A1 | 1/2006 | Lin et al. |

FOREIGN PATENT DOCUMENTS

WO    WO 03/055418    7/2003

OTHER PUBLICATIONS

Pickel et al., "The Effect of a Chewing Gum Containing Dicalcium Phosphate on Salivary Calcium and Phosphate", Ala. J. Med. Sci. 1965, vol. 2, pp. 286-287, no month.
Matsuya et al., "Effects of pH on the Reactions of Tetracalcium Phosphate and Dicalcium Phosphate", IADR Abstact 1991, no month.
Sugawara et al,, "Formation of Hydroxyapatite in Hydrogels from Tetracalcium Phosphate/Dicalcium Phosphate Mixtures," J. Nihon. Univ. Sch. Dent., 1989, vol. 31, pp. 372-381, no month.
Hong et al., The Periapical Tissue Reactions to a Calcium Phosphate Cement in the Teeth of Monkeys, J Biomed Mater Res. Apr. 1991, vol. 25(4), pp. 485-498.
DeRijk, et al., "Clinical Evaluation of a Hydroxyapatite Precipitate for the Treatment of Dentinal Hypersensitivity, Biomedical Engineering v. Recent Developments," Proc of 5th Southern Biomedical Engineering Conference, 1986, pp. 336-339. (Pergamon Press, New York), no month.
Groninger et al. "Evaluation of the Biocompatibility of a New Calcium Phosphate Setting Cement," J. Dent Res. 1984, 63 Abst. No. 270 (4 pages), no month.
Costantino et al., Evaluation of a New Hydroxyapatite Cement: Part III, Cranioplasty ina Cat Model, The Fifth Intl. Symposium on Facial Plastic Reconstructive Surgery of the Head and Neck, Toronto, Canada 1989. (18 pages), no month.
Shindo, et al., "Facial Skeletal Augmentation Using Hydroxyapatite Cement," Arch. Otolaryngol. Head Neck Surg. 1993, vol. 119, pp. 185-190, no month.
Briner et al., "Significance of Enamel Remineralization", J. Dent. Res. 1974, vol. 53, pp. 239-243, no month.
Silverstone, "Remineralization Phenomena", Caries Res. 1977, vol. 11 (Supp. 1), pp. 59-84, no month.
Costantino et al., "Hydroxyapatite Cement—Basic Chemistry and Histologic Properties," Arch. of Otolaryngology—Head & Neck Surgery, 1991, vol. 117, pp. 379-394, no month.
Friedman et al., "Hydroxyapatite Cement II. Obliteration and Reconstruction of the Cat Frontal Sinus," Arch. of Otolaryngology—Heady & Neck Surgery, 1991, vol. 117, pp. 385-389, no month.
Contantino et al., "Experimental Hydroxyapatite Cement Cranioplasty," Plastic and Reconstructive Surgery, 1992, vol. 90, No. 2, pp. 174-185, no month.
Miyazaki et al., "An Infrared Spectroscopic Study of Cement Formation of Polymeric Calcium Phosphate Cement," Jour of the Jap. Scoiety for Dent Mats & Devices, 1992, vol. II, No. 2. (8 pages), no month.
Driskell et al., "Development of Ceramic and Ceramic Composite Devices for Maxillofacial Applications", J. Biomed. Mat. Res. 1972, vol. 6, pp. 345-361, no month.
Hiatt et al., "Root Preparation I. Obduration of Dentinal Tubules in Treatment of Root Hypersensitivity", J. Periodontal, 1972, vol. 43, pp. 373-380, no month.
Patel et al., "Solubility of $CaHPO_4$ $2H_2O$ in the Quaternary System $Ca(OH)_2$—$H_3PO_4$—NaCl—$H_2O$ at 25° C.," J. Res. Nat. Bur. Stands. 1974, vol. 78A, pp. 675-681, no month.
Salyer et al., "Porous Hydroxyapatite as an Onlay Bone-Graft Substitute for Maxillofacial Surgery," Presented at the 54th Annual Scientific Meeting of the American Society of Plastic and Reconstructive Surgeons, Kansas City, Missouri, 1985, pp. 236-244, no month.
Kenney et al., "The Use of a Porous Hydroxyapatite Implant in Periodontal Defects," J. Periodontal, 1988, pp. 67-72, no month.
Zide et al., "Hydroxyapatite Cranioplasty Directly Over Dura," J. Oral Maxillofac Surg. 1987, vol. 45, pp. 481-486, no month.
Waite, et al., "Zygomatic Augmentation with Hydroxyapatite," J. Oral Maxillofac Surg 1986, pp. 349-352, no month.
Verwoerd, et al. "Porous Hydroxyapatite-perichondrium Graft in Cricoid Reconstruction, Acta Otolaryngol" 1987, vol. 103, pp. 496-502, no month.
Grote, "Tympanoplasty With Calcium Phosphate," Arch Otolaryngology 1984, vol. 110, pp. 197-199, no month.
Kent et al., "Alveolar Ridge Augmentation Using Nonresorbable Hydroxyapatite with or without Autogenous Cancellous Bone," J. Oral Maxillofac Surg 1983, vol. 41, pp. 629-642, no month.
Piecuch, "Augmentation of the Atrophic Edentulous Ridge with Porus Replamineform Hydroxyapatite (Interpore-200)", Dental Clinics of North America 1985, vol. 30(2), pp. 291-305, no month.
Misch, "Maxillary Sinus Augmentation for Endosteal Implants: Organized Alternative Treatment Plans," Int J Oral Implant 1987, vol. 4(2), pp. 49-58, no month.
Chohayeb, A. A. et al., "Evaluation of Calcium Phosphate as a Root Canal Sealer-Filler Material," J Endod 1987, vol. 13, pp. 384-386, no month.
Brown et al., "Crystallography of Tetracalcium Phosphate," Journal of Research of the National Bureau of Standards. A. Physics and Chemistry. 1965, vol. 69A, pp. 547-551, no month.
Sanin et al. "Particle Size Effects on pH and Strength of Calcium Phosphate Cement," IADR Abstract 1991, no month.
Chow et al., "X-ray Diffraction and Electron Microscopic Characterization of Calcium Phosphate Cement Setting Reactions," IADR Abstract, 1987. (1 page), no month.
Block et al. "Correction of Vertical Orbital Dystopia with a Hydroxyapatite Orbital Floor Graft," J. Oral Maxillofac Surg 1988, vol. 46, pp. 420-425, no month.
Brown, "Solubilities of Phosphates and Other Sparingly Soluble Compounds", Environmental Phosphorous Handbook 1973, pp. 203-239. (John Wiley & Sons, New York), no month.
Gregory et al., "Solubility of $CaHPO_4$ $2H_2O$ in the System $Ca(OH)_2$—$H_3PO_4$—$H_2O$ at 5, 15, 25, and 37.5° C.," J. Res. Nat. Bur. Stand. 1970, vol. 74A, pp. 461-475, no month.
Gregory et al., "Solubility of $\beta$—$Ca_3(PO_4)_2$ in the System $Ca(OH)_2$—$H_3PO_4$—$H_2O$ at 5, 15, 25 and 37° C.," J. Res. Nat. Bur. Stand., 1974, vol. 78A, pp. 667-674, no month.
McDowell et al., "Solubility of B—$Ca_5(PO_4)_3OH$ in the System $Ca(OH)_2$—$H_3PO_4$—$H_2O$ at 5, 15, 25 and 37° C.," J. Res. Nat. Bur. Stand. 1977, vol. 91A, pp. 273-281, no month.
McDowell et al., "Solubility Study of Calcium Hydrogen Phosphate. Ion Pair Formation," Inorg. Chem. 1971, vol. 10, pp. 1638-1643, no month.
Moreno et al., "Stability of Dicalcium Phosphate Dihydrate in Aqueous Solutions and Solubility of Octocalcium Phosphate," Soil Sci. Soc. Am. Proc. 1960, vol. 21, pp. 99-102, no month.
Chow et al, "Self-Setting Calcium Phosphate Cements," Mat. Res. Soc. Symp. Proc. pp. 3-23, no month.
Miyazaki et al., "Chemical Change of Hardened PCA/CPC Cements in Various Storing Solutions", The Journal of the Japanese Soc. for Dental Materials and Devices, 1992, vol. 11, No. 2, no month.
Fukase et al, "Thermal Conductivity of Calcium Phosphate Cement", IADR Abstract, 1990 (1 page), no month.
Sugawara et al. "Biocompatibility and Osteoconductivity of Calcium Phosphate Cement", IADR Abstract 1990. (1 page), no month.

Miyazaki et al., "Polymeric Calcium Phosphate Cements", IADR Abstract 1990. (1 page), no month.
Link et al., "Composite of Calcium Phosphate Cement and Genetically Engineered Protein Bioadhesive," IADR Abstract 1991. (1 page), no month.
Matsuya et al., "Effects of pH on the Reactions of Tetracalcium Phosphate and Dicalcium Phosphate", IADR Abstract 1991. (1 page), no month.
Briner et al., "Significance of Enamel Remineralization", J. Dent. Res. 1974, vol. 53, pp. 239-243, no month.
Chow, "Development of Self-Setting Calcium Phosphate Cements", Journal of The Ceramic Society of Japan, 1991, vol. 99 [10], pp. 954-964, no month.
Brown et al., A New Calcium Phosphate, Water Setting Cement, Cements Research Progress 1986, P. W. Brown, Ed., Westerville, Ohio: American Ceramic Society, 1988, pp. 352-379, no month.
Sugawara et al., "Evaluation of Calcium Phosphate as a Root Canal Sealer-Filler Material"IADR/AADR Abstract, 1987, (3 pages), no month.
Sugawara et al., "In Vitro Evaluation of the Sealing Ability of a Calcium Phosphate Cement When Used as a Root Canal Sealer Filler," J. Endodontics, 1989, vol. 16, pp. 162-165, no month.
Chow, "Calcium Phosphate Materials: Reactor Response" Adv Dent Res 1988, vol. 2(1), pp. 181-184, no month.
Fukase et al., "Setting Reactions and Compressive Strengths of Calcium Phosphate Cements", J Dent Res 1990, vol. 69(12), pp. 1852-1856, no month.
Miyazaki et al., "Chemical Change of Hardened PCA/CPC Cements in Various Storing Solutions", The Journal of the Japanese Soc. for Dental Materials and Devices, 1992, vol. 11, No. 2, pp. 48-64, no month.
U.S. Patent and Trademark Office, "Office communication" for U.S. Appl. No. 10/944,278 mailed Feb. 22, 2005 (8 pages).
Claims from Co-Pending U.S. Appl. No. 10/773,701, 3 pages.
Claims from Co-Pending U.S. Appl. No. 10/944,278, 3 pages.
Claims from Co-Pending U.S. Appl. No. 10/940,922, 4 pages.
Claims from Co-Pending U.S. Appl. No. 10/633,511, 5 pages.
Claims from Co-Pending U.S. Appl. No. 10/780,728, 6 pages.
Claims from Co-Pending U.S. Appl. No. 10/852,167, 7 pages.
Claims from Co-Pending U.S. Appl. No. 10/982,660, 3 pages.
Claims from Co-Pending U.S. Appl. No. 10/145,901, 3 pages.
Claims from Co-Pending U.S. Appl. No. 10/607,023, 1 page.
Sugawara et al., "Formation of Hydroxyapatite in Hydrogels from Tetracalcium Phosphate/Dicalcium Phosphate Mixtures," J. Nihon Univ. Sch. Dent., vol. 31, 372-381, 1989, no month.
Chow et al. "A Natural Bone Cement-A Laboratory Novelty Led to the Development of Revolutionary New Biomaterials", J. Res. Natl. Inst. Stand. Technol., 2001, vol. 106, pp. 1029-1033, no month.
Gburek et al., "Mechanical Activation of Tetracalcium Phsophate," J. Am. Ceramics Soc., vol. 87(2), pp. 311-313, no date.
International Search Report/Written Opinion for Intl. Application PCT/US04/369951, Examiner Baxter, mailed Jan. 4, 2006.
Office communication for U.S. Appl. No. 10/944,278 mailed Feb. 22, 2005.
Office communication for U.S. Appl. No. 11/129,063, mailed Jan. 13, 2005.
Office communication for U.S. Appl. No. 11/129,227, mailed Feb. 1, 2006.
Office communication for U.S. Appl. No. 11/131,892, mailed Nov. 15, 2005.
Office communication for U.S. Appl. No. 11/131,891, mailed Feb. 16, 2006.
Office communication for U.S. Appl. No. 11/132,167, mailed Nov. 15, 2005.
Office communication for U.S. Appl. No. 11/132,167, mailed Mar. 29, 2006.
Office communication for U.S. Appl. No. 11/133,166, mailed Nov. 15, 2005.
Office communication for U.S. Appl. No. 11/133,166, mailed Mar. 29, 2006.
Office communication for U.S. Appl. No. 11/137,112, mailed Nov. 15, 2005.
Office communication for U.S. Appl. No. 11/137,112, mailed May 20, 2005.
Office communication for U.S. Appl. No. 11/137,112, mailed Mar. 29, 2006.
Office communication for U.S. Appl. No. 11/137,695, mailed Dec. 20, 2005.
Office communication for U.S. Appl. No. 11/137,113, mailed Mar. 29, 2006.
Office communication for U.S. Appl. No. 11/137,113, mailed Nov. 15, 2005.
Office communication for U.S. Appl. No. 11/176,964, mailed Jan. 10, 2006.
Office communication for U.S. Appl. No. 11/176,963, mailed Jan. 10, 2006.
Chow et al. "A Natural Bone Cement-A Laboratory Novelty Led to the Development of Revolutionary New Biomaterials", J. Res. Natl. Inst. Stand. Technol., 2001, vol. 106, pp. 1029-1033, no month.
Gburek et al., "Mechanical Activation of Tetracalcium Phsophate," J. Am. Ceramics Soc., vol. 87(2), pp. 311-313, no month.

CALCIUM PHOSPHATE CEMENTS MADE FROM (TTCP) WITH SURFACE WHISKERS AND PROCESS FOR PREPARING SAME

CROSS-REFERENCE TO RELATED APPLICATIONS

This is a continuation application of, and claims the benefit of priority under 35 USC § 120 to, U.S. patent application Ser. No. 10/773,701, filed Feb. 6, 2004, pending, which is a continuation-in-part application of U.S. patent application Ser. No. 10/607,023, filed Jun. 27, 2003, U.S. Pat. No. 6,960,249, which is a continuation-in-application of U.S. patent application Ser. No. 10/414,582, filed Apr. 16, 2003, U.S. Pat. No. 7,094,282, which is a continuation-in-part application of U.S. patent application Ser. No. 09/615,384, filed Jul. 13, 2000, now abandoned. This application also claims priority to U.S. patent application Ser. No. 10/328,019, filed Dec. 26, 2002, now U.S. Pat. No. 6,840,995, which claims the benefit of priority to U.S. patent application Ser. No. 09/351,912, filed Jul. 14, 1999, now U.S. Pat. No. 6,379,453B1. The prior applications are commonly assigned with the present invention and are incorporated herein by reference.

BACKGROUND OF THE INVENTION

1. Field of the Invention

The present invention relates to a tetracalcium phosphate (TTCP) for producing fast-setting, bioresorbable calcium phosphate cements (CPC), and in particular, to a tetracalcium phosphate having whiskers on the surface thereof for producing fast-setting, bioresorbable CPC having a high initial strength.

2. Description of the Related Art

U.S. Pat. No. 6,379,453B1 which is commonly assigned with the present invention discloses a process for producing a fast-setting, bioresorbable calcium phosphate cement comprising the following steps: obtaining a powder mixture from at least one calcium phosphate selected from the group consisting of $Ca_4(PO_4)_2O$, $Ca(HPO_4)_2H_2O$, $CaHPO_4$, $Ca_8H_2(PO_4)_6 \cdot 5H_2O$, $\alpha\text{-}Ca_3(PO4)_2$, $\beta\text{-}Ca_3(PO_4)_2$, $Ca_2P_2O_7$, $Ca_2H_2P_2O_8$, wherein the molar ratio of Ca to P in the mixture is roughly between 1 and 2; mixing the powder mixture in a phosphate-containing solution to obtain a powder/solution mixture having a concentration of less than 4 g powder mixture per ml solution; immediately heating the powder/solution mixture to a temperature of roughly 50° C.–350° C. to obtain a powder containing uniformly distributed submicron-sized apatite crystals; and mixing the apatite crystal-containing powder in a phosphate ion-containing solution to obtain a fast-setting, bioresorbable calcium phosphate cement.

SUMMARY OF THE INVENTION

An extensive study on the preparation of the fast-setting, bioresorbable calcium phosphate cement disclosed in U.S. Pat. No. 6,379,453B1 has been conducted by the same inventors and their co-workers, and found that a fast-setting, bioresorbable CPC having a high initial strength can be prepared from a unique calcium phosphate, tetracalcium phosphate ($Ca_4(PO_4)_2O$, TTCP) particle having basic whiskers or fine crystals on the surface thereof, wherein said basic whiskers or fine crystals have a Ca/P ratio greater than 1.33. Therefore an object of the invention is to provide such a unique TTCP particle. Another object of the present invention is to provide a process for preparing said unique TTCP particle. A further object of the present invention is to provide a fast-setting, bioresorbable CPC calcium phosphate cement prepared from said unique TTCP particle.

The invention accomplishes the above object by providing a tetracalcium phosphate ($Ca_4(PO_4)_2O$, TTCP) particle having basic calcium phosphate whiskers on a surface of said TTCP particle; said basic calcium phosphate whiskers having a length up to about 5000 nm and a width up to about 500 urn, and preferably, a length from about 1 nm to about 2000 nm and a width from about 1 nm to about 200 rim. Said basic calcium phosphate whiskers have a Ca/P molar ratio greater than 1.33, and preferably greater than 1.35 and less than 4.0. Said basic calcium phosphate whiskers have a non-stoichiometric chemical composition. Further, said basic calcium phosphate whiskers are substantially free of a hydroxyapatite phase, and comprises TTCP as a major phase.

DETAILED DESCRIPTION OF THE INVENTION

Figure 1A:
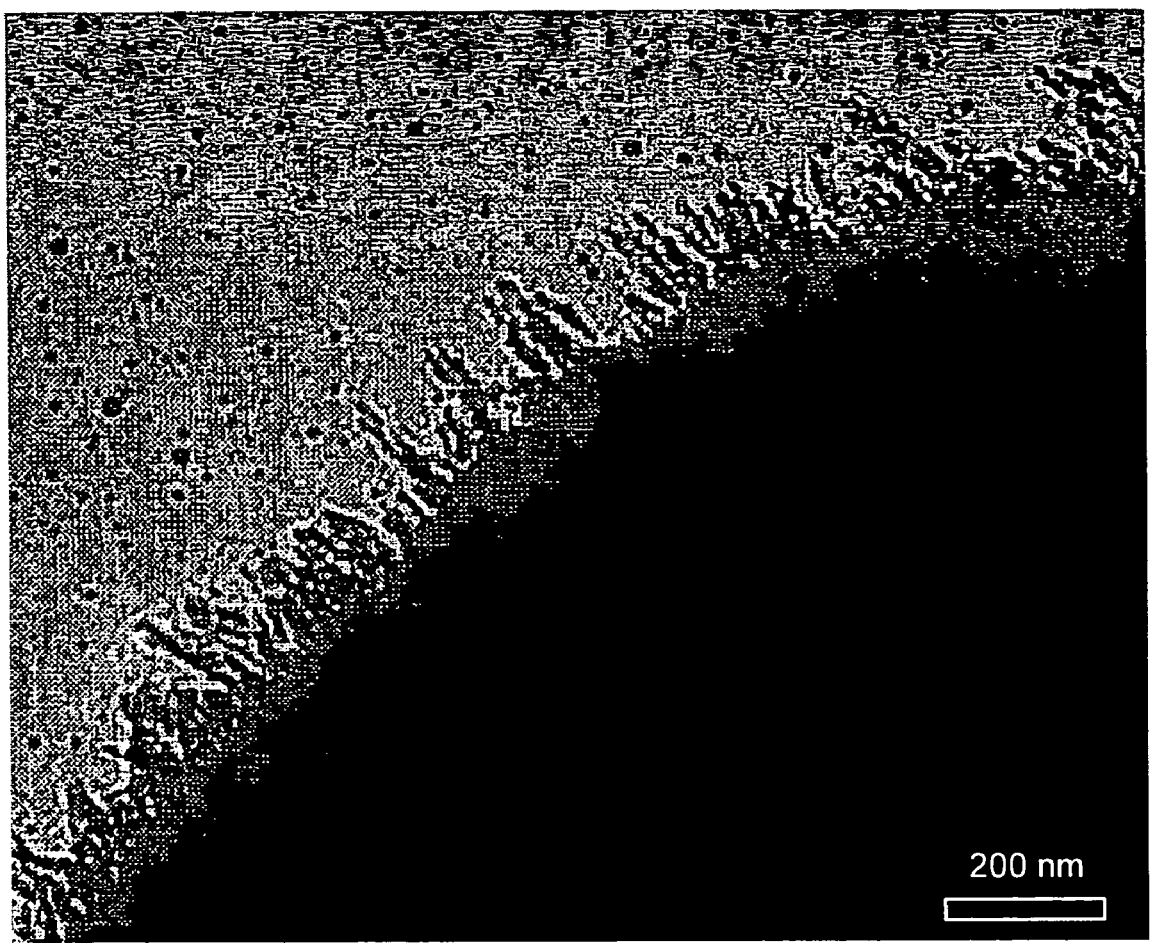
FIGS. 1A to 1C are related to microstructure and diffraction pattern of calcium phosphate whiskers grown on TTCP surface according to the present invention, wherein (a) bright field image of whiskers; (b) electron diffraction pattern of whiskers; and (c) interpretation of the diffraction pattern.

The present invention discloses a process for preparing a tetracalcium phosphate (TTCP) powder comprising TTCP particles comprising basic calcium phosphate whiskers on surfaces of said TTCP particles, said process comprising the following steps:

a) mixing a TTCP powder with a whisker-inducing solution so that basic calcium phosphate whiskers start to grow on surfaces of TTCP particles of said TTCP powder;

b) terminating the growth of said calcium phosphate whiskers by drying the whisker-inducing solution in the mixture, so that said calcium phosphate whiskers have a length up to about 5000 nm and a width up to about 500 nm, and preferably, a length from about 1 nm to about 2000 nm and a width from about 1 nm to about 200 nm, said basic calcium phosphate whiskers have a Ca/P molar ratio greater than 1.33, preferably greater than 1.35 and less than 4.0, and said basic calcium phosphate whiskers have a non-stoichiometric chemical composition, preferably said basic calcium phosphate whiskers are substantially free of a hydroxyapatite phase, and comprises TTCP as a major phase.

Optionally, at least one additive selected from the group consisting of sodium phosphate ($Na_3PO_4$), disodium hydrogen phosphate ($Na_2HPO_4$), sodium dihydrogen phosphate ($NaH_2PO_4$), disodium hydrogen phosphate dodecahydrate ($Na_2HPO_4 \cdot 12H_2O$), disodium hydrogen phosphate heptahydrate ($Na_2HPO_4 \cdot 7H_2O$), sodium phosphate dodecahydrate ($Na_3PO_4 \cdot 12H_2O$), orthophosphoric acid ($H_3PO_4$), calcium sulfate ($CaSO_4$), $Ca_4(PO_4)_2O$, $CaHPO_4 \cdot 2H_2O$, $CaHPO_4$, $Ca_8H_2(PO_4)_6 \cdot 5H_2O$, alpha-$Ca_3(PO_4)_2$, beta-$Ca_3(PO_4)_2$, $Ca_2P_2O_7$, and $Ca_2H_2P_2O_8$, $(NH_4)_3PO_4$, $(NH_4)_2HPO_4$, and $(NH_4)H_2PO_4$ together with said TTCP particles are mixed with the whisker-inducing solution in step a).

Optionally, said drying in step b) is carried out by heating the mixture resulting from step a) at a temperature less than about 1000° C. Preferably, said drying in step b) comprises separating the mixture resulting from step a) and heating the separated powder at a temperature of about 50 to 500° C.

The heating includes (but not limited to) the conventional oven/furnace heating, resistance heating, infrared heating, microwave heating, electron beam heating, ion beam heating, laser beam heating and plasma heating. Preferably said heating is conducted in vacuum, inert atmosphere or air atmosphere.

The whisker-inducing solution in step a) may be an acidic aqueous solution, a basic aqueous solution, an organic solvent or a substantially pure water. The acidic aqueous solution may contain at least one Ca or P source, or is free from Ca and P. The acidic aqueous solution can be selected from the group consisting of nitric acid ($HNO_3$), hydrochloric acid (HCl), phosphoric acid ($H_3PO_4$), carbonic acid ($H_2CO_3$), sodium dihydrogen phosphate ($NaH_2PO_4$), sodium dihydrogen phosphate monohydrate, sodium dihydrogen phosphate dihydrate, potassium dihydrogen phosphate ($KH_2PO_4$), ammonium dihydrogen phosphate ($NH_4H_2PO_4$), malic acid, acetic acid, lactic acid, citric acid, malonic acid, succinic acid, glutaric acid, tartaric acid, oxalic acid and their mixture.

The basic aqueous solution for use as the whisker-inducing solution in the method of the present invention may contain at least one Ca or P source, or is substantially free from Ca and P. The basic aqueous solution may be selected from the group consisting of ammonia, ammonium hydroxide, alkali metal hydroxide, alkali earth hydroxide, disodium hydrogen phosphate ($Na_2HPO_4$), disodium hydrogen phosphate dodecahydrate, disodium hydrogen phosphate heptahydrate, sodium phosphate dodecahydrate ($Na_3PO_4 \cdot 12H_2O$), dipotassium hydrogen phosphate ($K_2HPO_4$), potassium phosphate tribasic ($K_3PO_4$), diammonium hydrogen phosphate (($NH_4)_2HPO_4$), ammonium phosphate trihydrate (($NH_4)_3PO_4 \cdot 3H_2O$), sodium bicarbonate ($NaHCO_3$), and their mixture.

Preferably, said whisker-inducing solution in step a) is a basic aqueous solution. More preferably, said basic aqueous solution is a diammonium hydrogen phosphate (($NH_4)_2HPO_4$), $Na_2HPO_4$, or $K_2HPO_4$ aqueous solution. A suitable diammonium hydrogen phosphate (($NH_4)_2HPO_4$) aqueous solution has a concentration of at least 5 wt %, preferably 10–60 wt %, based on the weight of said solution, and the mixing of said TTCP powder with this diammonium hydrogen phosphate (($NH_4)_2HPO_4$) aqueous solution in step a) is in a ratio of less than about 10 g powder per ml solution, preferably less than about 5 g powder per ml solution. In one of the preferred embodiment of the present invention, said concentration is about 33 wt %, and the mixing ratio is about 1 gm TTCP per 13 ml solution.

The present invention also discloses a calcium phosphate cement (CPC) powder comprising the TTCP powder of the present invention.

The following examples are intended to demonstrate the invention more fully without acting as a limitation upon its scope, since numerous modifications and variations will be apparent to those skilled in this art.

TTCP Preparation

The TTCP powder was fabricated in-house from the reaction of dicalcium pyrophosphate ($Ca_2P_2O_7$) (Sigma Chem. Co., St. Louis, Mo., USA) and calcium carbonate ($CaCO_3$) (Katayama Chem. Co., Tokyo, Japan) using the method suggested by Brown and Epstein [*Journal of Research of the National Bureau of Standards—A Physics and Chemistry* 6 (1965) 69A 12].

TEM Examination

A Hitachi Model-HF2000 200 kV field emission transmission electron microscope (TEM) equipped with a Noran Vayager Model 1000 energy dispersive spectroscopy (EDS) system was used for the study. The aperture size for microchemical analysis (Ca/P ratio) is 15 nm.

EXAMPLE 1

Whisker-Inducing Treatment of TTCP Particles Treated in Phosphate-Containing Basic Solution $Ca_4(PO_4)_2O$ (TTCP) powder as synthesized was sieved with a #325 mesh. The sieved powder has an average particle size of about 10 gin. An aqueous solution of diammonium hydrogen phosphate was prepared by dissolving 20 g of diammonium hydrogen phosphate, (NH4)2HOP4, in 40 ml deionized water. The resulting solution had a pH value of 8.02. To the TTCP powder the basic aqueous solution of diammonium hydrogen phosphate was added according to the ratio of 1 gm TTCP/13 ml solution. The TTCP powder was immersed in the basic aqueous solution for various periods of time of 1 minute, 5 minutes and 10 minutes, and filtered rapidly with a vacuum pump again. The resulting powder cake was dried in an oven at 50° C. The dried powder was dispersed in ethanol with supersonication. A drop of the dispersion was dripped on a single-side carbon sieve of #325 mesh having a diameter of 3 mm, and left dry to obtain a specimen coated with a thin carbon film for electrical conductivity for TEM examination. The microchemical analysis (Ca/P ratio) results often specimens (P1 to P10) for each treat time are shown in Table 1.

TABLE 1

| Treat time | Ca/P | | | | | | | | | | | | Whisker width (nm) | Whisker width (nm) |
| --- | --- | --- | --- | --- | --- | --- | --- | --- | --- | --- | --- | --- | --- | --- |
| | P1 | P2 | P3 | P4 | P5 | P6 | P7 | P8 | P9 | P10 | Avg. | SD* | | |
| 1 min | 1.20 | 1.30 | 1.26 | 1.14 | 1.12 | 1.03 | 1.22 | 1.19 | 1.14 | 1.25 | 1.19 | 0.08 | <50 | <100 |
| 5 min | 1.85 | 1.61 | 1.35 | 1.76 | 1.40 | 1.52 | 1.63 | 1.53 | 1.35 | 1.38 | 1.54 | 0.17 | <100 | <300 |
| 10 min | 3.81 | 3.20 | 1.78 | 1.74 | 1.80 | 1.38 | 1.61 | 1.81 | 2.01 | 1.63 | 2.08 | 0.78 | <100 | <300 |

*SD = standard deviation
*SD = standard deviation

Figure 1B:
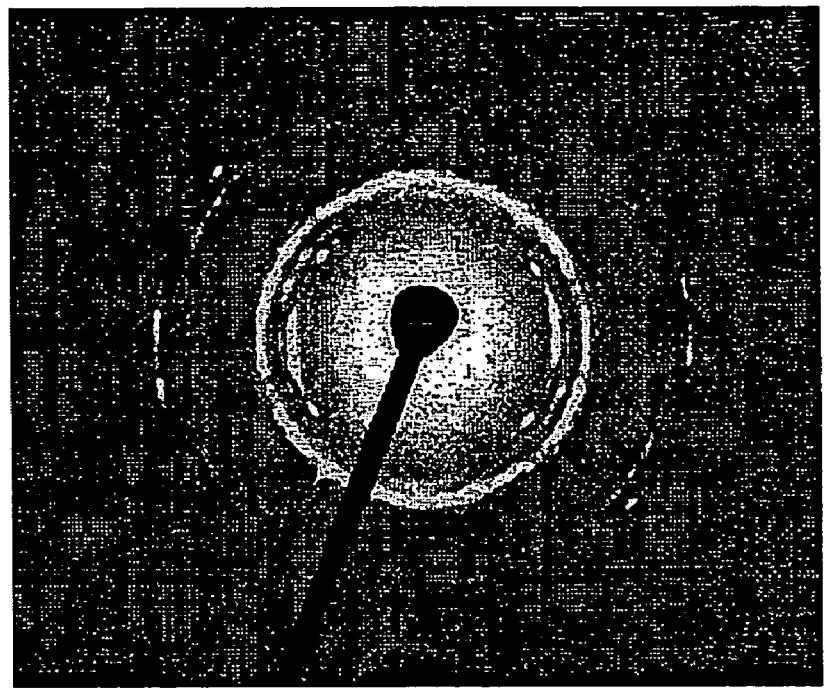
Figure 1C:
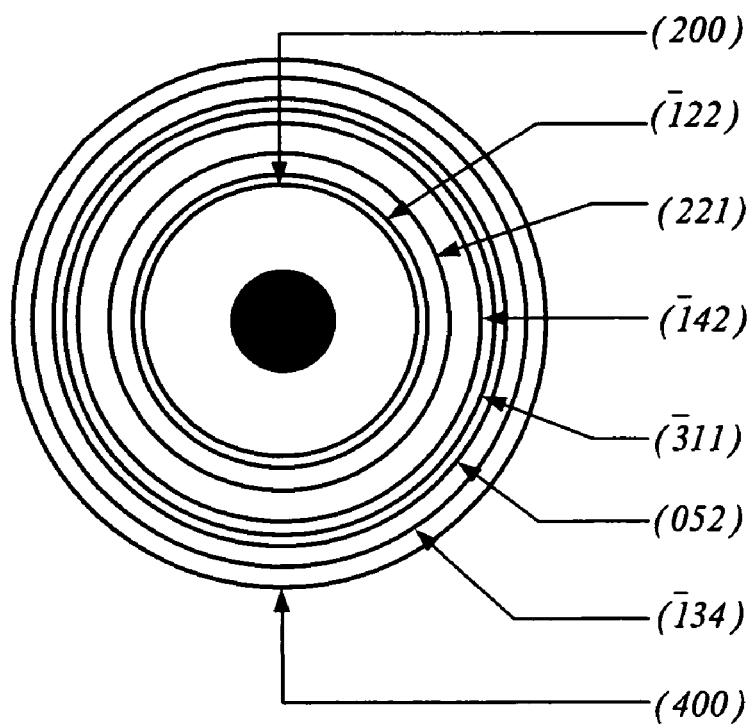

FIG. 1 represents a typical microstructure of the calcium phosphate whiskers grown on TTCP surface under such condition. FIG. 1A is a bright-field image showing the whiskers are substantially radial-oriented and the majority of which have lengths <300 um and widths <100 nm; FIG. 1B is a typical electron diffraction pattern of such whiskers. The dotted-ring pattern is a direct result of the diffraction of numerous nano-sized whiskers; FIG. 1C is the indexing/interpretation of the diffraction pattern, which clearly shows that every ring matches a certain crystallographic plane of TTCP phase, indicating the whiskers have a TTCP crystal structure. The absence of hydroxyapatite (HA) phase (100) ring (d=0.817 nm) in the diffraction pattern excludes the possibility for the whiskers to have an apatite crystal structure under this whisker treatment condition. It also can be seen from Table 1 that basic calcium phosphate whiskers have a Ca/P ratio other than 1.67, i.e. a non-stoichiometric chemical composition. The Ca?P ratio of hydroxyapatite (HA) is 1.67. The results show that Ca/P ratio is sensitive to the process condition (in this case, treating time).

EXAMPLE 2

Whisker-Inducing Treatment of TTCP Particles Treated in Phosphate-Containing Acidic Solution The procedures of Example 1 were repeated except that the basic aqueous solution was changed to 1M phosphorus acid aqueous solution having a pH of 0.8 and the immersion time was changed to 30 seconds. The results are shown in Table 2.

TABLE 2

| Treat time | Ca/P | | | | | | | | | | | | Whisker width (nm) | Whisker length (nm) |
| --- | --- | --- | --- | --- | --- | --- | --- | --- | --- | --- | --- | --- | --- | --- |
| | P1 | P2 | P3 | P4 | P5 | P6 | P7 | P8 | P9 | P10 | Avg | SD* | | |
| 30 sec | 3.73 | 2.0 | 2.28 | 1.41 | 2.65 | 1.43 | 1.77 | 1.89 | 1.65 | 1.54 | 2.04 | 0.71 | <200 | <600 |

*SD = standard deviation

EXAMPLE 3

Whisker-Inducing Treatment Of TTCP Particles Treated in Phosphate-Free Basic Solution The procedures of Example 1 were repeated except that the basic aqueous solution was changed to a basic aqueous NaOH solution having a pH of 10.66 and the immersion time was changed to 30 seconds and 24 hours. For the specimens treated for 30 seconds no whisker was observed on TTCP surface. The results for the treat time of 24 hours are shown in Table 3.

TABLE 3

| Treat time | Ca/P | | | | | | | | | | | | Whisker width (nm) | Whisker length (nm) |
| --- | --- | --- | --- | --- | --- | --- | --- | --- | --- | --- | --- | --- | --- | --- |
| | P1 | P2 | P3 | P4 | P5 | P6 | P7 | P8 | P9 | P10 | Avg | SD* | | |
| 24 hr | 1.90 | 2.19 | 2.80 | 3.40 | 1.47 | 2.05 | 1.53 | 1.63 | 1.42 | 2.03 | 2.04 | 0.63 | <200 | <600 |

*SD = standard deviation

EXAMPLE 4

Whisker-Inducing Treatment of TTCP Particles Treated In Phosphate-Free Acidic Solution The procedures of Example 1 were repeated except that the basic aqueous solution was changed to 0.1 6M HCl aqueous solution having a pH of 0.8 and the immersion time was changed to 30 seconds, 10 minutes, one hour and 24 hours. For the specimens treated for 30 seconds no whisker was observed on TTCP surface. The results for the remaining treat times are shown in Table 4.

TABLE 4

| Treat time | Ca/P | | | | | | | | | | | | Whisker width (nm) | Whisker width (nm) |
| --- | --- | --- | --- | --- | --- | --- | --- | --- | --- | --- | --- | --- | --- | --- |
| | P1 | P2 | P3 | P4 | P5 | P6 | P7 | P8 | P9 | P10 | Avg. | SD* | | |
| 10 min | 1.61 | 1.92 | 1.40 | 1.52 | 1.52 | | | | | | | | <50 | <100 |
| 1 hr | 1.41 | 1.90 | 1.52 | 1.67 | 1.57 | 1.42 | 1.53 | 1.46 | 1.38 | 1.60 | 1.55 | 0.15 | <100 | <200 |
| 24 hr | 2.65 | 1.53 | 1.61 | 1.77 | 1.52 | 2.23 | 1.36 | 1.83 | 1.44 | 2.09 | 1.80 | 0.41 | <200 | <600 |

*SD = standard deviation

EXAMPLE 5

Compressive Strength of CPC Prepared from the Whisker-Grown TTCP Particles $Ca_4(PO_4)_2O$ (TTCP) powder as synthesized was sieved with a #325 mesh and has an average particle size of about 10 gm. To the sieved TTCP powder a HCl aqueous solution having a pH of 0.8 was added according to the ratio of 1 gm TTCP/13 ml solution. The sieved TTCP powder was immersed in the HCl solution for 12 hours, filtered rapidly and washed with deionized water, and filtered rapidly with a vacuum pump again. The resulting powder cake was dried in an oven at 50° C. The dried powder was divided into halves, ground for 20 minutes and 120 minutes separately, and combined. A setting solution of diammonium hydrogen phosphate was prepared by dissolving 20 g of diammonium hydrogen phosphate, $(NH_4)_2HPO_4$, in 40 ml deionized water. 100 g of the mixed ground powder and 35 ml of the setting solution were well mixed to form a paste, which was then filled in molds to form specimens for compression test. The specimens were removed from the molds 15 minutes after the mixing, and soaked in a Hanks' solution. The soaked specimens were removed from the Hanks' solution at various periods of soaking time, and were immediately subjected to the compression test without drying. The compression test was conducted according to a method commonly used in the literature. The cylindrical samples have a diameter of 6 mm and a length of 12 mm. Results: compressive strength is 27.4 MPa for the soaking time of 20 minutes, and 48 MPa for one-day soaking time.

EXAMPLE 6

Compressive Strength of CPC Prepared from the Whisker-Grown TTCP Particles $Ca_4(PO_4)_2O$ (TTCP) powder as synthesized was sieved with a #325 mesh and has an average particle size of about 10 gm. To the sieved TTCP powder the aqueous $(NH_4)_2HPO_4$ solution prepared in Example 1 was added according to the ratio of 1 gm TTCP/13 ml solution. The sieved TTCP powder was immersed in the $(NH_4)_2HPO_4$ solution for 5 minutes, filtered rapidly and washed with deionized water, and filtered rapidly with a vacuum pump again. The resulting powder cake was dried in an oven at 50° C. The dried powder was ground 120 minutes to obtain a powder A. The procedures in Example 5 were repeated to obtain a powder B except that the dried powder was ground ordy for a period of 300 minutes. A mixed powder of A and B in a ratio of 1:1 ratio was subjected to the compression tests following the procedures recited in Example 5. Results: compressive strength is 26 MPa for the soaking time of 20 minutes, and 42.8 MPa for one-day soaking time.

EXAMPLE 7

Compressive Strength Of CPC Prepared From The Whisker-Grown TTCP Particles

The procedures in Example 5 were repeated except that the HCl solution was changed to the aqueous $(NH_4)_2HPO_4$ solution prepared in Example 1 and the soaking time was changed to 5 minutes. Results: compressive strength is 18.6 MPa for the soaking time of 20 minutes, and 48.8 MPa for one-day soaking time.

EXAMPLE 8

Compressive Strength of CPC Prepared from the Whisker-Grown TTCP Particles $Ca_4(PO_4)_2O$ (TTCP) powder as synthesized was sieved with a #325 mesh and ground for two hours. To the ground TTCP powder the powder B prepared in Example 5 was added and mixed in a ratio of 1:1. The resulting mixed powder was subjected to the compression tests following the procedures recited in Example 5. Results: compressive strength is 19.7 MPa for the soaking time of 20 minutes, and 43.6 MPa for one-day soaking time.

EXAMPLE 9

X-Ray Diffraction Of Whisker-Treated TTCP Powder and Immersed CPC Prepared from Such TTCP A TTCP powder was whisker-treated for 5 minutes according to the process described in Example 1. X-ray diffraction (XRD) was performed using an X-ray diffractometer (Rigaku D-max IIIV, Tokyo, Japan) with Ni-filtered CuKα radiation operated at 30 kV and 20 mA at a scanning speed of 1°/min. The phases were identified by matching each characteristic XRD peak with that compiled in JCPDS files.

Figure 2:
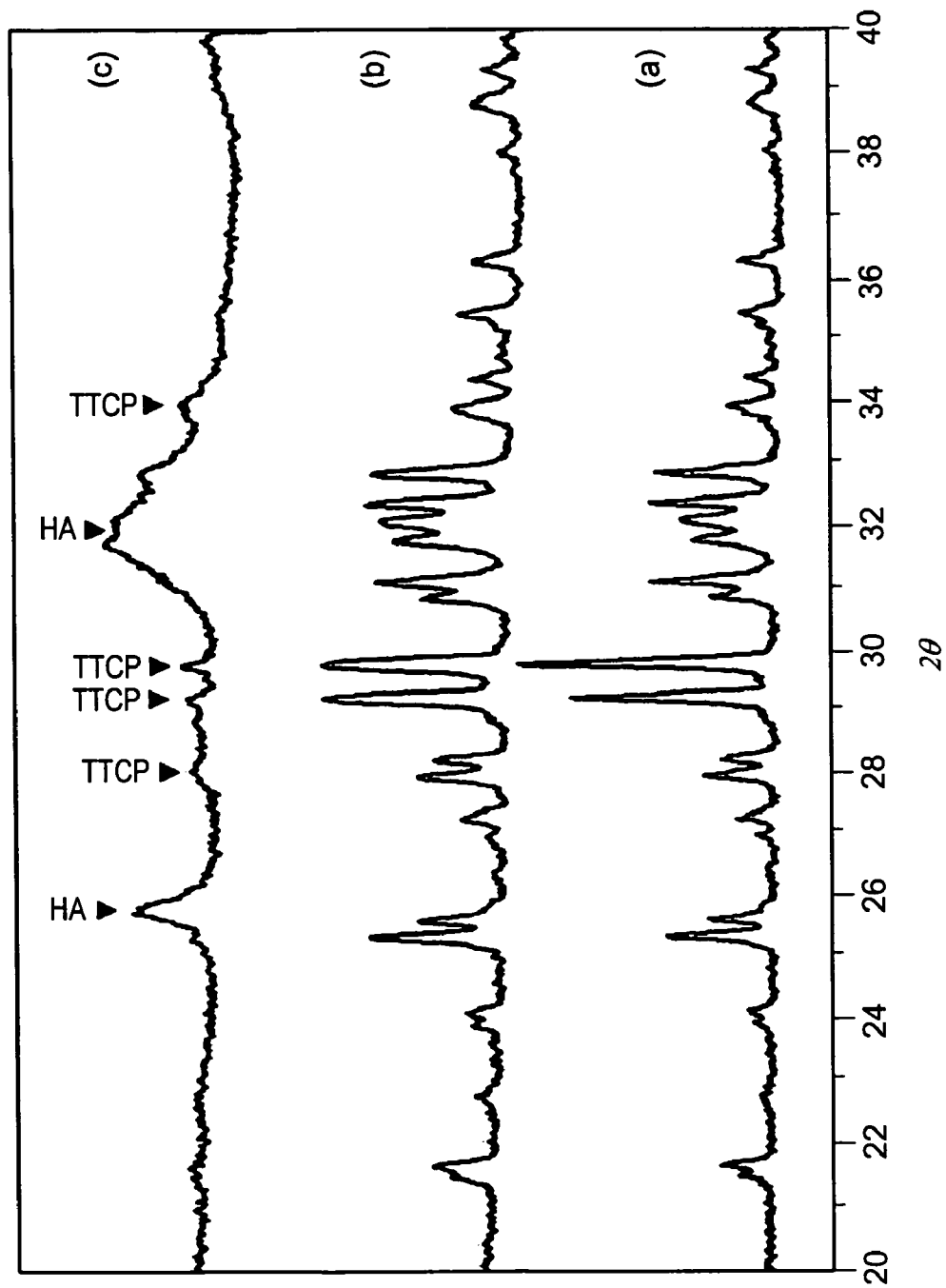
FIG. 2 shows XRD patterns, wherein (a) TTCP without whisker treatment; (b) TTCP with whisker treatment in $(NH_4)_2HPO_4$ for 5 minutes; and (c) CPC prepared from whisker-treated TTCP powder immersed in Hanks' solution for 24 hours.

Results: As indicated in FIG. 2, the XRD pattern of the whisker-treated TTCP powder (b) is substantially identical to that of TTCP as synthesized (a). The perfect match of every XRD peak position (diffraction angle) with the JCPDS data indicates that there is no additional phase formed during the whisker treatment. 0.7 g whisker-treated TTCP powder with 0.25 ml setting solution to form a CPC paste. The setting solution was prepared by dissolving 20 g $(NH_4)_2HPO_4$ in 40 ml deionized water. The CPC paste was filled in a cylindrical mold (12 mm in height and 6 mm in diameter), allowing hardening of the paste to occur within the mold. After 15 minutes the hardened CPC sample was removed from the mold and immersed in a 37° C. Hanks' solution for 24 hours. After removing from the Hanks' solution and drying, the CPC sample was ready for XRD analysis. After immersion in Hanks' solution for 24 hours, the XRD pattern (c) of the CPC shows a large amount of HA phase which has replaced TTCP as the dominant phase. At this time only a small amount of TTCP remains. The result suggests that the CPC prepared from the whisker-treated TTCP powder of the invention can quickly transform into HA (the major component of human bone), once implanted.

EXAMPLE 10

Setting Solution Prepared From $(NH_4)H_2PO_4$ and KOH

A TTCP powder was whisker-treated for 5 minutes according to the process described in Example 1. The resulting powder cake was dried in an oven at 50° C. The dried powder was ground for 120 minutes. A setting solution was prepared by dissolving 13.2 g $(NH_4)H_2PO_4$ in 40 ml deionized water to obtain an initial solution having a pH value of 3.72, and adding KOH to the initial solution so that the pH value was adjusted to 7.5. 100 g of the ground powder and 35 ml of the setting solution were well mixed to form a paste for 1 minute, which was then filled in molds to form specimens for compression tests following the procedures recited in Example 5. Results: compressive strength is 9.6 MPa for the soaking time of 20 min.

EXAMPLE 11

Setting Solution Prepared from $(NH_4)H_2PO_4$ And NaOH

The procedures in Example 10 were repeated except that the KOH was changed to NaOH and the final pH value of the setting solution was 7.8, and 20 ml of the setting solution was mixed with 100 g of the ground powder. Results: compressive strength is 10.3 MPa for the soaking time of 20 min.

EXAMPLE 12

Setting Solution Prepared from $(NH_4)HPO_4$, $NaH_2PO_4 \cdot 2H_2O$ and $K_2HPO_4$ A TTCP powder was prepared following the procedures recited in Example 10. A setting solution was prepared by dissolving 7.5 g $(NH_4)_2HPO_4$, 2.5 g $NaH_2PO_4 \cdot 2H_2O$ and 5 g $K_2HPO_4$ in 40 ml deionized water. The final pH value of the setting solution was 7.56. 100 g of the ground powder and 30 ml of the setting solution were well mixed to form a paste for 1 minute, which was then filled in molds to form specimens for compression tests following the procedures recited in Example 5. Results: compressive strength is 18.0 MPa for the soaking time of 20 min.

EXAMPLE 13

Setting Solution Prepared From $Na_2HPO_4 \cdot 12H_2O$, $NaH_2PO_4 \cdot 2H_2O$ and $(NH_4)_2HPO_4$ A TTCP powder was prepared following the procedures recited in Example 10. A setting solution was prepared by dissolving 3 g $Na_2HPO_4 \cdot 12H_2O$, 3 g $NaH_2PO_4 \cdot 2H_2O$ and 7.5 g $(NH_4)_2HPO_4$ in 40 ml deionized water. The final pH value of the setting solution was 7.38. 100 g of the ground powder and 30 ml of the setting solution were well mixed to form a paste for 1 minute, which was then filled in molds to form specimens for compression tests following the procedures recited in Example 5. Results: compressive strength is 20.8 MPa for the soaking time of 20 min.

EXAMPLE 14

Setting Solution Prepared from Phosphoric Acid and Ammonia

Solution

A TTCP powder was prepared following the procedures recited in Example 10. A setting solution was prepared by mixing 37.68 ml of 85 wt % phosphoric acid and 100 ml deionized water, and then 73.8 ml of 28 wt % ammonia solution. The final pH value of the setting solution was 7.0. 100 g of the ground powder and 30 ml of the setting solution were well mixed to form a paste for 1 minute, which was then filled in molds to form specimens for compression tests following the procedures recited in Example 5. Results: compressive strength is 23.4 MPa for the soaking time of 20 min.

Although a "basic" whisker can be grown on TTCP surface by immersion in a variety of solutions, the process should be carefully controlled. For example, when the solution contains a P source in the absence of Ca, the immersion time should be long enough to grow a basic whisker (an "acidic" whisker is grown at the early stage due to the excess P ions in the solution). Yet the immersion time should not be too long either to avoid the basic whisker's growing too large, that can largely deteriorate the CPC properties.

On the other hand, when the solution does not contain P (e.g., HCl), acidic whisker is never grown on the surface of TTCP particles. All the observed whiskers on TTCP particles at all stages are basic in nature.

In addition to Ca/P ratio, the growth rate of a basic whisker is also sensitive to such process parameters as the type, pH, temperature and ion concentrations of the solution, to name a few.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A calcium phosphate cement made by the process comprising:
   contacting tetracalcium phosphate (TTCP) particles with a whisker-inducing liquid for a period of time such that whiskers having a length of up to about 5000 nm and a width of up to about 500 nm form on the surface of at least a portion of the TTCP particles, wherein the whiskers comprise basic calcium phosphate comprising TTCP as the major phase, and wherein the Ca/P molar ratio of the basic calcium phosphate comprising the whiskers is at least about 1.33;
   separating the TTCP particles from the whisker-inducing liquid; and
   contacting the TTCP particles with a setting solution.

2. The calcium phosphate cement of claim 1, wherein the whisker inducing liquid comprises an acidic solution.

3. The calcium phosphate cement of claim 1, wherein the whisker inducing liquid comprises nitric acid ($HNO_3$), hydrochloric acid (HCl), phosphoric acid ($H_3PO_4$), carbonic acid ($H_2CO_3$), sodium dihydrogen phosphate ($NaH_2PO_4$), sodium dihydrogen phosphate monohydrate, sodium dihydrogen phosphate dihydrate, potassium dihydrogen phosphate ($KH_2PO_4$), ammonium dihydrogen phosphate ($NH_4H_2PO_4$), malic acid, acetic acid, lactic acid, citric acid, malonic acid, succinic acid, glutaric acid, tartaric acid, oxalic acid or mixtures thereof.

4. The calcium phosphate cement of claim 1, wherein the whisker inducing liquid comprises a source of phosphate ions.

5. The calcium phosphate cement of claim 1, wherein the whisker inducing liquid comprises phosphoric acid.

6. The calcium phosphate cement of claim 1, wherein the whisker inducing liquid comprises hydrochloric acid.

7. The calcium phosphate cement of claim 1, wherein the whisker inducing liquid comprises a basic solution.

8. The calcium phosphate cement of claim 1, wherein the whisker inducing liquid comprises ammonia, ammonium hydroxide, alkali metal hydroxide, alkali earth hydroxide, disodium hydrogen phosphate ($Na_2HPO_4$), disodium hydrogen phosphate dodecahydrate, disodium hydrogen phosphate heptahydrate, sodium phosphate dodecahydrate ($Na_3PO_4 \cdot 12H_2O$), dipotassium hydrogen phosphate ($K_2HPO_4$), potassium phosphate tribasic ($K_3PO_4$), diammonium hydrogen phosphate (($NH_4)_2HPO_4$), ammonium phosphate trihydrate (($NH_4)_3PO_4 \cdot 3H_2O$), sodium bicarbonate ($NaHCO_3$), or mixtures thereof.

9. The calcium phosphate cement of claim 1, wherein the whisker inducing liquid comprises a source of ammonium ions.

10. The calcium phosphate cement of claim 1, wherein the whisker inducing liquid comprises a source of potassium ions.

11. The calcium phosphate cement of claim 1, wherein the whisker inducing liquid comprises a source of sodium ions.

12. The calcium phosphate cement of claim 1, wherein the whisker inducing liquid comprises diammonium hydrogen phosphate.

13. The calcium phosphate cement of claim 1, wherein the whisker inducing liquid comprises sodium hydroxide.

14. The calcium phosphate cement of claim 1, wherein the ratio of TTCP particles to whisker inducing liquid is less than about 10 g/ml.

15. The calcium phosphate cement of claim 1, wherein the ratio of TTCP particles to whisker inducing liquid is less than about 5 g/ml.

16. The calcium phosphate cement of claim 1, wherein the TTCP particles are contacted with the whisker inducing liquid for up to about 24 hours.

17. The calcium phosphate cement of claim 1, wherein the TTCP particles are contacted with the whisker inducing liquid for between about 1 minute to about 10 minutes.

18. The calcium phosphate cement of claim 1, further comprising mixing an additive with the TTCP particles, wherein contacting the TTCP particles with the whisker inducing liquid comprises contacting the mixture of TTCP particles and the additive with the whisker inducing liquid.

19. The calcium phosphate cement of claim 18, wherein the additive comprises sodium phosphate ($Na_3PO_4$), disodium hydrogen phosphate ($Na_2HPO_4$), sodium dihydrogen phosphate ($NaH_2PO_4$), disodium hydrogen phosphate dodecahydrate ($Na_2HPO_4 \cdot 12H_2O$), disodium hydrogen phosphate heptahydrate ($Na_2HPO_4 7H_2O$), sodium phosphate dodecahydrate ($Na_3PO4.12H_2O$), orthophosphoric acid ($H_3PO_4$), calcium sulfate ($CaSO_4$), $Ca_4(PO_4)_2O$, $CaHPO_4 \cdot 2H_2O$, $CaHPO_4$, $Ca_8H_2(PO_4)_6 \cdot 5H_2O$, alpha-$Ca_3(PO_4)_2$, beta-$Ca_3(PO_4)_2$, $Ca_2 {}_{P_2}O_7$, and $Ca_2H_2P_2O_8$, $(NH_4)_3PO_4$, $(NH_4)_2HPO_4$, and $(NH_4)H_2PO_4$, or mixtures thereof.

20. The calcium phosphate cement of claim 1, wherein the pH of the setting solution is between about 7.0 to about 7.8.

21. The calcium phosphate cement of claim 1, wherein separating the TTCP particles from the whisker-inducing liquid comprises heating the TTCP particles to a temperature of up to about 1000° C.

22. The calcium phosphate cement of claim 1, wherein separating the TTCP particles from the whisker-inducing liquid comprises heating the TTCP particles to a temperature of between about 50° C. to about 500° C.

* * * * *

UNITED STATES PATENT AND TRADEMARK OFFICE
CERTIFICATE OF CORRECTION

PATENT NO. : 7,204,876 B2  
APPLICATION NO. : 11/133165  
DATED : April 17, 2007  
INVENTOR(S) : Lin et al.

Page 1 of 1

It is certified that error appears in the above-identified patent and that said Letters Patent is hereby corrected as shown below:

Claim 19, col. 11, line 12, please delete "$Ca_{2p2}O_7$" and substitute therefor --"$Ca_2 P_2 O_7$"--.

Signed and Sealed this

Tenth Day of July, 2007

JON W. DUDAS  
*Director of the United States Patent and Trademark Office*